United States Patent [19]

Scribner et al.

[11] Patent Number: 5,054,492

[45] Date of Patent: Oct. 8, 1991

[54] ULTRASONIC IMAGING CATHETER HAVING ROTATIONAL IMAGE CORRELATION

[75] Inventors: Robert M. Scribner; Stephen M. Salmon, both of Sunnyvale; Mark L. Pomeranz, Los Gatos, all of Calif.

[73] Assignee: Cardiovascular Imaging Systems, Inc., Sunnyvale, Calif.

[21] Appl. No.: 628,745

[22] Filed: Dec. 17, 1990

[51] Int. Cl.$^5$ .............................................. A61B 8/12
[52] U.S. Cl. ........................ 128/662.06; 128/660.09; 128/660.04
[58] Field of Search ...................... 128/662.06, 662.03, 128/660.04, 663.01; 606/194; 604/96, 103

[56] References Cited

U.S. PATENT DOCUMENTS

| 4,567,896 | 2/1986 | Barnea et al. | 128/660.07 |
| 4,794,931 | 1/1989 | Yock | 128/660.03 |
| 4,821,731 | 4/1989 | Martinelli et al. | 128/662.06 |
| 4,911,173 | 3/1990 | Terwilliger | 128/662.06 |
| 4,951,677 | 8/1990 | Crowley et al. | 128/662.06 |

OTHER PUBLICATIONS

Medi-Tech, Inc., Watertown, Mass., designated Ultrasound Imaging Catheter Catalog No. 01-118.

Primary Examiner—Francis Jaworski
Assistant Examiner—George Manuel
Attorney, Agent, or Firm—Townsend and Townsend

[57] ABSTRACT

An ultrasonic imaging catheter comprises a catheter body having a distal end and a proximal end. An ultrasonic imaging transducer is located within the distal end and is arranged to produce an image in an image plane which is generally normal to the axial direction of the catheter. An ultrasonically opaque element is attached to the catheter body and disposed through the image plane so that an image artifact or marker appears on the resulting ultrasonic image. The artifact corresponds to the location on the catheter where the element is located. A fluoroscopic marker is also provided on the catheter body, typically located proximally of the region where the ultrasonic imaging transducer and other components are located. The fluoroscopic marker has a geometry selected so that the marker has a unique appearance depending on the rotational orientation of the catheter when viewed by fluoroscopy. In this way, the viewing physician may determine the actual rotational orientation of the catheter within the body lumen being viewed and may further correlate the position of the catheter with the apparent position of the ultrasonic image which has been obtained.

31 Claims, 3 Drawing Sheets

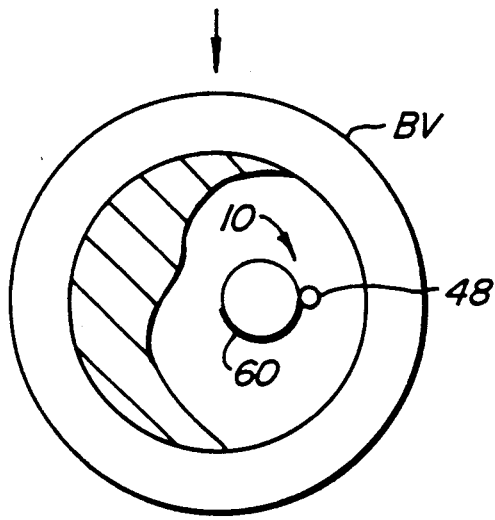
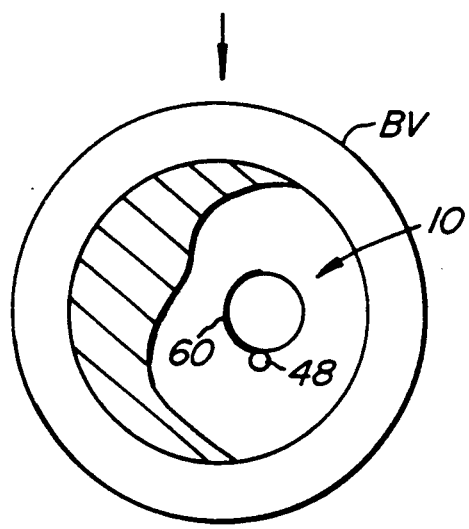
FIG. 6B.  FIG. 6C.
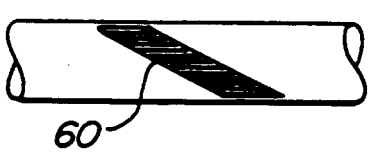
FIG. 7B.  FIG. 7C.
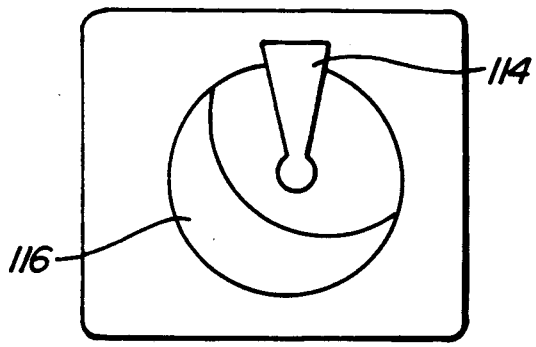
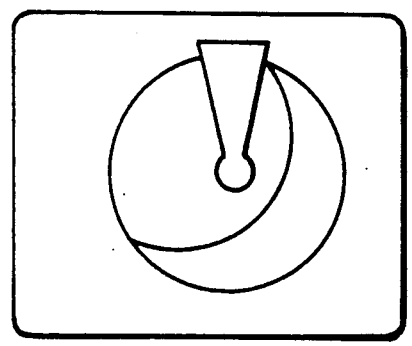
FIG. 8B.  FIG. 8C.

ULTRASONIC IMAGING CATHETER HAVING ROTATIONAL IMAGE CORRELATION

BACKGROUND OF THE INVENTION

1. Field of the Invention

The present invention relates generally to the construction and use of ultrasonic imaging catheters, and more particularly to imaging catheters having reference markers which permit rotational correlation of an ultrasonic cross-sectional image produced by the catheter with a fluoroscopic planar image of the catheter within a hollow body organ, particularly a blood vessel.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels that feed the heart. When deposits accumulate in localized regions of the blood vessels, blood flow is restricted and the person's health is at serious risk.

Numerous approaches for reducing and removing such vascular deposits have been proposed, including balloon angioplasty, where a balloon-tipped catheter is used to dilitate a stenosed region within the blood vessel; atherectomy, where a blade or other cutting element is used to sever and remove the stenotic material; and laser angioplasty, where laser energy is used to ablate at least a portion of the stenotic material.

In order to more effectively direct such interventional techniques, a variety of vascular imaging devices and methods have been proposed. Of particular interest to the present invention, intraluminal imaging catheters having ultrasonic transducers at their distal end have been employed to produce cross-sectional images of a stenotic region from within a blood vessel.

The ability to produce in situ cross-sectional images of a diseased blood vessel is advantageous in several respects. First, such images permit qualitative assessment of the nature of the stenotic region in order to help select the most effective treatment modality. Of particular concern to the present invention, the cross-sectional visual information may be used to evaluate the non-symmetric nature of a stenotic region so that intervention can be directed only at regions where the stenotic material occurs and not at healthy regions of the blood vessel where the interventional procedure might cause damage. Stenotic deposits often grow eccentrically so that a given cross-section of the blood vessel may be occluded over one portion of the wall while the remaining portion of the wall is free of disease. In such cases, it is important to localize potentially damaging treatment modalities, such as laser ablation and atherectomy, only at those regions of the blood vessel wall where the stenotic material is present.

Heretofore, it has been difficult to precisely correlate the orientation of a cross-sectional image produced by an ultrasonic imaging catheter with the actual spatial orientation of the image features within the blood vessel. Many imaging catheter constructions provide no information at all relative to the rotational orientation of the catheter within the blood vessel while the image is being produced. In such cases, correlation of the image with the actual orientation of the blood vessel is difficult or impossible. While other catheter constructions include a structural member which crosses the image plane of the ultrasonic imaging device (which produces an observable artifact on the ultrasonic image), it is still difficult to correlate position of the image artifact with the actual orientation of the catheter within the blood vessel.

It would therefore be desirable to provide improved ultrasonic imaging catheters and methods for their use which would facilitate correlation of an ultrasonic cross-sectional image with the physical orientation of the catheter producing such image within a blood vessel or other body organ. In this way, regions of the blood vessel requiring therapy could be precisely located and targeted for subsequent interventional treatment. It would be further desirable if the improved catheter and method permitted such correlation to be made by fluoroscopic observation of the catheter, such as that which is employed during initial catheter placement. It would be particularly desirable if the rotational orientation of the catheter could be uniquely determined by fluoroscopic observation at any time so that the catheter orientation could be correlated with a real time ultrasonic image being produced. Most preferably, such improvements should require only minor modification of proven catheter designs so that the other functions of the catheters are substantially undisturbed.

2. Description of the Relevant Art

U.S. Pat. No. 4,794,931, to Yock (assigned to the assignee of the present invention) describes an ultrasonic imaging catheter having a rotating transducer or a rotating mirror in combination with a fixed transducer. The imaging components are located within a housing which may be ultrasonically opaque. No specific features are provided for correlating the image produced by the catheter with the rotational orientation of the catheter. U.S. Pat. No. 4,821,731, describes the use of externally generated transverse magnetic fields which are used in determining rotational orientation of an imaging catheter.

Copending application Ser. No. 07/422,935, assigned to the assignee of the present invention but naming a different inventive entity, describes an ultrasonic imaging catheter having a fixed transducer and a rotating mirror. In one embodiment of the catheter, the cross-sectional image plane of the rotating mirror is free from ultrasonically opaque obstructions except for an axial tube which receives a movable guide wire which bypasses the imaging components. The axial tube will produce a rotationally-aligned image artifact on the cross-sectional image produced by the catheter.

Medi-tech, Inc., Watertown, Massachusetts, produces a catheter designated Ultrasound Imaging Catheter Catalog No. 01-118 having a rotating transducer mounted within its distal end. The catheter body circumscribing the rotating transducer is ultrasonically transparent, but provisions are made for a movable guide wire to pass through the image plane of the transducer. The guide wire will produce an image artifact when in place during an imaging procedure.

SUMMARY OF THE INVENTION

According to the present invention, ultrasonic imaging catheters comprise a catheter body having a proximal end and a distal end. An ultrasonic transducer is mounted within the distal end of the catheter body and is arranged to produce a cross-sectional image in an image plane generally normal to the longitudinal axis of the catheter body. In the preferred embodiments, the transducer is arranged to rotate by itself or to operate in combination with a rotating mirror to mechanically sweep an ultrasonic signal about the image plane. Phased array transducer designs may also find use. Such imaging catheters are used to produce intraluminal images within blood vessels and other hollow body organs.

The imaging catheter will be used in combination with a monitor and associated conventional circuitry to produce a two-dimensional image of the blood vessel or other hollow body organ on a monitor screen. The two-dimensional image will reveal the surrounding contour of tissue, atheroma deposits, secondary structure, and other structural information relevant to treatment and diagnosis of various diseased conditions. There is nothing inherent in the two-dimensional image, however, which allows the apparent orientation of the image to be correlated with the actual orientation of the observed features within the blood vessel or other hollow body organ. Because the rotational orientation of the catheter within the lumen is random, the apparent orientation of the image on the screen is also random.

The catheter of the present invention overcomes this deficiency by providing two additional pieces of information to the treating physician. First, a marker or artifact is produced on the ultrasonic image which appears on the monitor screen, where the position of the marker corresponds to a fixed radial direction relative to the distal tip of the catheter. By locating this marker on the ultrasonic image, the physician will be able to precisely determine the orientation of the distal tip of the catheter relative to the features which are revealed in the image. This information, however, by itself is still insufficient to allow determination of the absolute orientation of the features relative to the blood vessel or other hollow body organ within the patient.

In order to determine such absolute orientation of the features on the image, the catheter includes a second marker which is visible under conventional fluoroscopic observation and which allows the physician to determine the absolute orientation of the distal tip of the catheter relative to the body organ. The second marker will be spaced longitudinally away from the transducer and any associated mirror since such components will interfere with fluoroscopic visibility. Conveniently, the marker may be a fluoroscopically opaque stripe formed on the outside of the catheter body on either side of the imaging components. The stripe will have a particular geometry which is selected to produce a pattern which uniquely corresponds to the rotational orientation of the catheter when viewed under fluoroscopy. In this way, the orientation of the distal end of the catheter body may be determined by viewing the pattern of the marker by fluoroscopy. Once the rotational position of the distal end of the catheter is known, the absolute orientation of the features viewed on the ultrasonic image may be determined relative to the catheter orientation using the ultrasonic marker which appears on the ultrasonic image. Knowledge of the true orientation of the observed structural features facilitates subsequent treatment and diagnosis of the blood vessel or other hollow body organ.

BRIEF DESCRIPTION OF THE DRAWINGS

FIGS. 6A–6C illustrate the catheter of FIGS. 1 and 2 located within the lumen of a blood vessel at different rotational orientations.

FIGS. 7A–7C illustrate the appearance of the fluoroscopic stripe on the catheter as it would appear under the various rotational orientations illustrated in FIGS. 6A–6C.

FIGS. 8A–8C illustrate the ultrasonic images which would appear on a monitor screen when the catheter is at each of the rotational orientations illustrated in FIGS. 6A–6C.

DESCRIPTION OF THE SPECIFIC EMBODIMENTS

Figure 1:
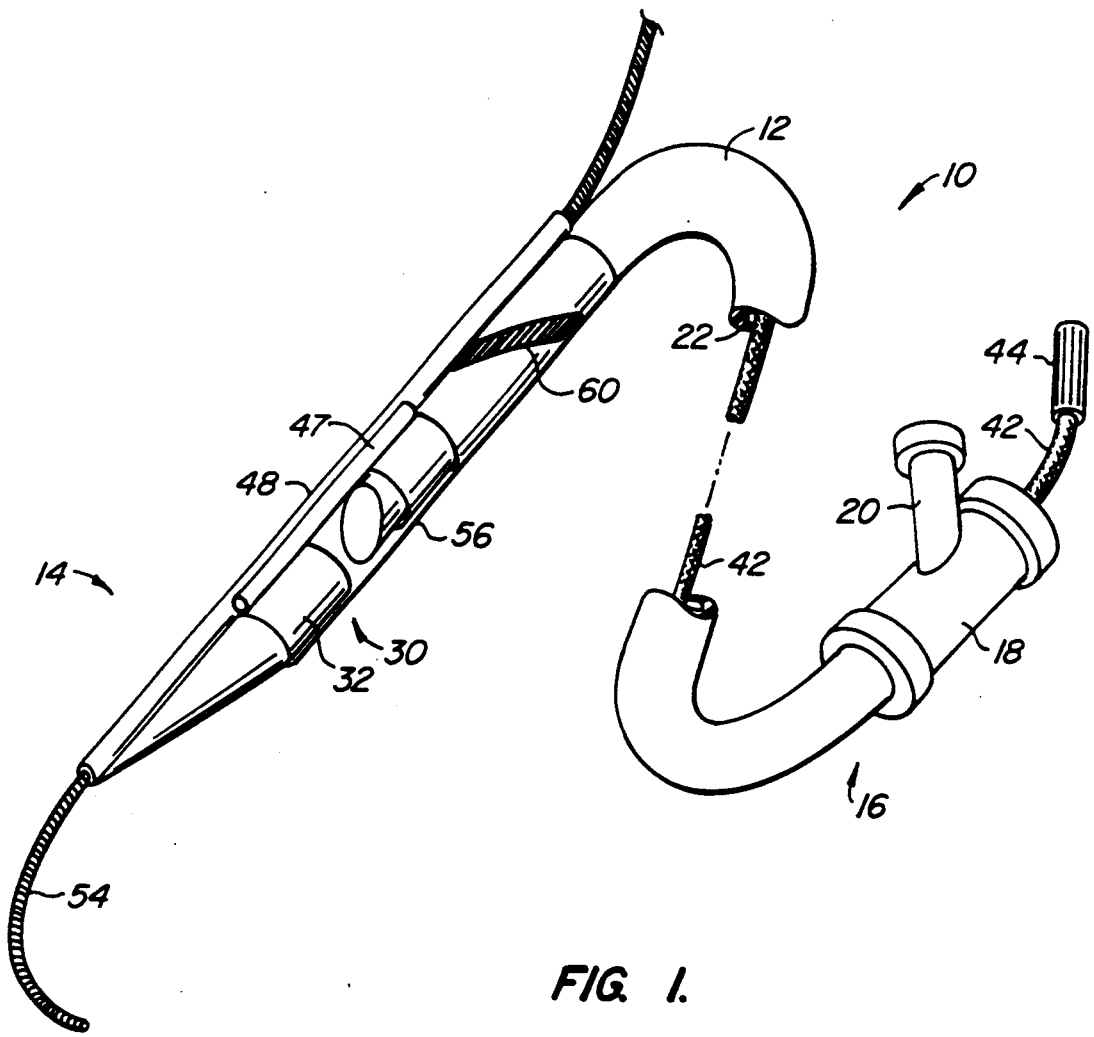
FIG. 1 is a perspective view of a first embodiment of a catheter constructed in accordance with the principles of the present invention.

Ultrasonic imaging catheters constructed in accordance with the principles of the present invention will comprise an elongate catheter body having a proximal end and a distal end. The catheter body will include at least one ultrasonic transducer located at or near the distal end, and the transducer will be arranged to produce a two-dimensional cross-sectional image in an image plane normal to the catheter body when used with conventional signal processing circuitry and monitors. In order to facilitate correlation of the two-dimensional image with the actual orientation of features within a lumen being imaged, the catheter is provided with means for producing two rotational reference markers. The first reference marker is produced on the ultrasonic image and is aligned with a fixed radial direction relative to the distal end of the catheter body. Using this marker, the relative orientation of the distal end of the catheter body and the features revealed on the two-dimensional image can be obtained. The second marker is visible under conventional fluoroscopic imaging and allows precise determination of the orientation of the distal end of the catheter within the lumen. Using these two pieces of information, the apparent orientation of the features on the two-dimensional image can be precisely correlated with the actual orientation within the patient's lumen.

Catheters according to the present invention will find their greatest use in imaging the interior walls of blood vessels, particularly to determine the nature and structure of stenotic regions within the blood vessels prior to interventional treatment, such as balloon angioplasty, atherectomy, laser ablation, and the like. The design and use of intravascular ultrasonic imaging catheters are described in U.S. Pat. Nos. 4,794,931 and 3,938,502, the disclosures of which are incorporated herein by reference. The ultrasonic imaging catheters of the present invention may also find use in imaging other body lumens found in different hollow body organs and ducts, such as the urinary tract, cystic duct, and the like.

The structure of the catheter body will vary depending on the intended application. For vascular catheters, the catheter body will comprise one or more flexible tubular members having axial lumens formed therein. The catheter body will be suitable for insertion into and manipulation within a patient's vascular system using techniques which are now well known in the medical community so that the distal region of the catheter body may be brought to a desired location within the vascular system.

The catheter body may be composed of a wide variety of biologically compatible materials, typically being made from natural or synthetic polymers, such as silicone, rubber, natural rubber, polyethylene, polyvinylchloride, polyurethanes, polyesters, polytetrafluoroethylenes (PTFE), and the like. Frequently, a catheter body may be formed as a composite having a reinforcement material incorporated within the polymeric body in order to enhance its strength, flexibility, and toughness. Suitable enforcement layers include wire mesh layers, and the like. The flexible tubular members of the catheter body will normally be formed by extrusion, with one or more integral lumens being provided. If desired, the catheter diameter can be modified by heat expansion and shrinkage using conventional techniques. Particular techniques for forming the vascular catheters of the present invention are well described in the patent and medical literature.

The overall dimensions of the catheter will depend on use, with the length of vascular catheters varying widely, typically between about 40 cm and 150 cm, usually being between about 40 cm and 120 cm, for peripheral catheters and being between about 110 cm and 150 cm for coronary catheters. The diameter of the catheter body may also vary widely, with the diameter typically being between about 3 French (F; 1 F=0.33 mm) and 6 F.

The ultrasonic transducer mounted within the distal end of the catheter body is arranged to emit and receive ultrasonic energy within an imaging plane disposed normally to the axial direction of the catheter. A variety of conventional ultrasonic transducer arrangements are suitable for use in the present invention. For example, phased-array ultrasonic transducers may be arranged as described in U.S. Pat. No. 3,938,502, the disclosure of which has been previously incorporated herein by reference. Preferably, however, the ultrasonic transducer(s) will be arranged to mechanically rotate or sweep a continuous ultrasonic signal about the imaging plane. Such rotation of the signal can be achieved in several ways. For example, the transducer itself can be rotated, typically using an external drive motor which is attached by means of a flexible drive shaft running the length of the transducer. Alternatively, the transducer can be fixed and an associated mirror or other reflective surface rotated to deflect the ultrasonic signal radially outward. As a second alternative, the transducer and mirror can be mounted in tandem and simultaneously rotated to achieve radial deflection and sweeping of the ultrasonic signal. The latter two arrangements are generally preferred for use in the present invention since they allow an increased focal length and reduce the imaging "ring down" affect, improving imaging quality.

The ultrasonic transducer and other imaging component(s) may be mounted within a housing which is formed contiguously with the distal end of the catheter body. The housing may be rigid or flexible. The use of a rigid housing is preferred when the imaging system uses a rotating mirror and a fixed ultrasonic transducer. With such a design, it is necessary to maintain a fixed spatial relationship between the mirror and the transducer. Such a fixed relationship can be obtained by mounting the transducer, mirror, and other components within a rigid housing which holds the components relative to each other.

The reference marker or artifact in the ultrasonic image may be produced in a variety of ways. Most simply, an ultrasonically opaque element may be attached to the distal end of the catheter body so that it passes through the ultrasonic imaging plane. In this way, a shadow will be produced in the ultrasonic image, where the position of the shadow corresponds precisely to the position of the element on the distal end of the catheter body. Thus, the physician viewing the image on the monitor will be able to correlate the precise rotational orientation of the catheter relative to the features which are revealed in the image. Conveniently, the opaque element may be a structural member which forms part of the catheter or housing. In a preferred embodiment, the structural member is a rigid tube or rod which joins a distal and a proximal portion of the housing together.

The ultrasonic reference marker may also be produced electronically. For example, with a rotating transducer and/or mirror, an electrical contact may be provided which is tripped every time the rotating components pass through a fixed radial direction. The momentary contact can be used to create a marker or artifact in the ultrasonic image which corresponds to the radial direction. A similar electronic marker could be introduced into the circuitry for a phased array transducer. Other approaches for generating the ultrasonic reference marker for the present invention will be apparent to those skilled in the art.

The fluoroscopic reference marker will be formed as a physical component on the catheter body itself. Conveniently, a stripe or other insignia will be disposed on the exterior of the catheter body so that the outline or "footprint" of the marker is clearly visible when the catheter is being viewed by conventional fluoroscopic techniques. The geometry of the stripe or other insignia will be selected so that it forms a distinct pattern in the fluoroscopic image depending on the rotational orientation of the distal end of the catheter body. For example, a diagonal stripe may be formed or imprinted on the catheter body, where the stripe has the geometry of a spiral arc in three dimensions. Such a spiral arc will have a unique appearance at each angle of rotation of the distal end of the catheter. Similarly, an L-shaped insignia can be formed on the exterior of the catheter body and will have a unique appearance depending on the angle of rotation of the catheter. Many other geometries might also find use.

Such external stripes and insignia may be applied to the catheter body by conventional techniques such as those used for forming fluoroscopic rings on intravascular catheters. The stripe or other insignia will typically be formed using a heavy metal foil, such as gold or platinum, and will be bonded to the exterior of the catheter body using heat or a suitable adhesive, typically by embedding the foil into the catheter body using heat. The marker will usually be encapsulated within a thin sheath, typically by heat shrinking polyethylene or other suitable thermoplastic over the exterior of the catheter body.

Figure 2:
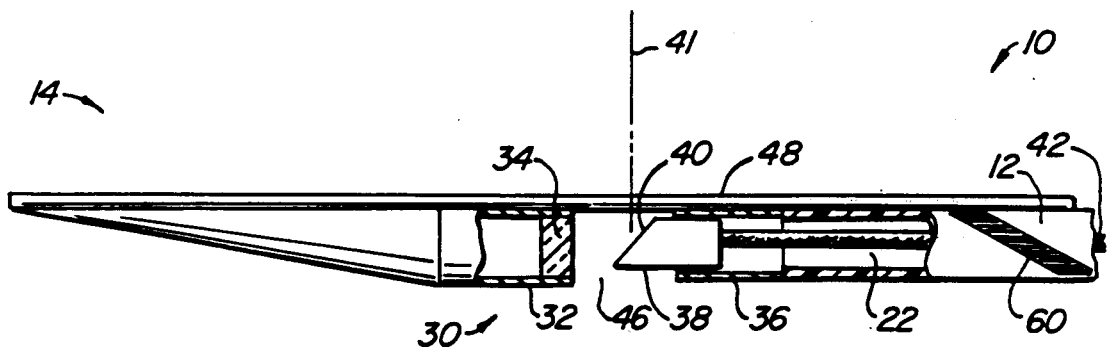
FIG. 2 is an enlarged view of the distal end of the catheter of FIG. 1, with portions broken away.

Referring now to FIGS. 1 and 2, a first embodiment 10 of the catheter of the present invention will be described. The catheter 10 includes a flexible catheter body 12 having a distal end 14 and a proximal end 16. A proximal housing 18 is secured to the proximal end 16 of the catheter body 12 and includes a side port 20 which is connected to an axial lumen 22 extending the length of catheter body 12. Using side port 20, the interior of the catheter 10 can be filled with a suitable medium for enhancing the transmission of ultrasonic energy, such as saline. Preferably, the ultrasound medium will be fluoroscopically transparent so that viewing of the second reference marker will not be impaired.

The catheter 10 includes a distal housing 30 formed contiguously with the distal end of the catheter body 12. The housing 30 includes a distal shield 32 holding an ultrasonic transducer 34 and a proximal bearing retainer 36 which receives a rotatable mirror 38 having an inclined reflective surface 40. The reflective surface 40 is typically inclined at an angle of about 45° in order to deflect ultrasonic energy from the transducer 34 radially outward in an imaging plane 41 (FIG. 2) which is generally normal to the axial direction of the distal end of the catheter 10.

The mirror 38 is attached to a flexible drive shaft 42 which extends in the proximal direction through axial lumen 22 and out through the proximal end of housing 18, where it terminates in a spindle element 44. The spindle allows coupling of the drive shaft 42 into an electric drive motor capable of driving the mirror. Suitable drive motors are described and illustrated in U.S. Pat. No. 4,771,774, the disclosure of which is incorporated herein by reference.

The housing 30 includes a gap region 46 located between the distal transducer shield and the proximal bearing retainer 36. The imaging plane defined by mirror 38 passes through this gap in order to minimize interference with the ultrasonic image from the housing. A connecting member 47, however, passes axially through the image plane and acts to rigidly join the transducer shield 32 to the bearing retainer 36. The connecting member 47 may be a tube or a rod formed from an ultrasonically opaque material, such as stainless steel, so that it will provide an image artifact or shadow in the ultrasonic image which is produced by the catheter. Such an artifact or shadow will always be located in the same radial direction relative to the distal end 14 of the catheter 10. Thus, such shadow or artifact can be used to determine the relative alignment of the catheter and the image which is produced.

In the preferred embodiment, a separate tube 48 forms a guide wire lumen and is typically formed from a flexible material to facilitate manipulation of the catheter within the vascular system. As illustrated in FIG. 1, a movable guide wire 54 may be received in a continuous lumen which is defined by the tube 48. A transparent sheath 56 (FIG. 1) will be formed about the housing 30 and the proximal end of the catheter body 12 in order to close the gap 46 to retain the liquid medium which is used to fill the medium. The sheath 56 is typically formed from polyethylene or other ultrasonically transparent material and may be applied by conventional heat shrink techniques.

It will be appreciated that it would be possible to utilize the rigid element 47 as a portion of the guide wire tube 48, in which case the element 47 would be in the form of a tube joined at its distal and proximal ends to flexible tubular regions. It has been found, however, that use of a flexible guide wire tube separate from the rigid element is preferable since the transition between rigid and flexible regions of the guide wire lumen can constrict the passage of a guide wire therethrough.

An inclined stripe 60 is formed on the exterior of the distal end of catheter body 12. As the stripe is formed over the outer cylindrical surface of the catheter body 12, its actual geometry will be in the nature of a spiral or helical arc. The stripe will be formed from metal foil, as previously described, and will typically be protected by the sheath 56 which extends proximally over the stripe. As described in more detail hereinafter, the inclined stripe 60, when viewed under a fluoroscope, will have a unique apparent geometry which allows the viewing physician to determine the rotational orientation of the catheter within the body lumen in which it has been placed.

Figure 3:
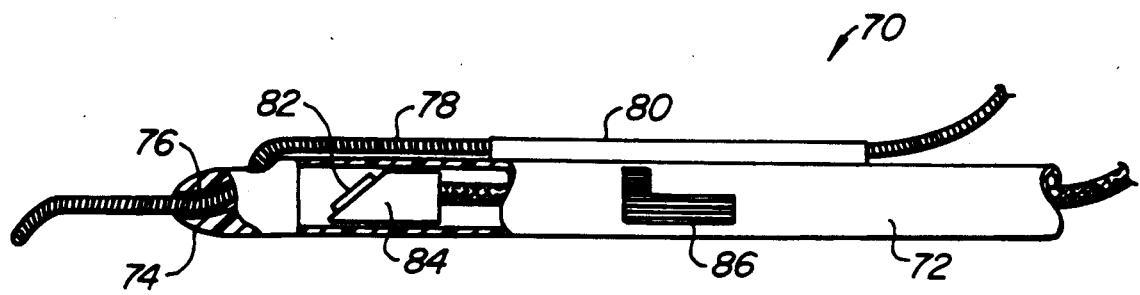
FIG. 3 illustrates the distal end of a second embodiment of a catheter constructed in accordance with the principles of the present invention.

Referring now to FIG. 3, an alternate embodiment 70 of a catheter constructed in accordance with the principles of the present invention will be described. The catheter 70 includes a catheter body 72 which extends from a proximal end (not illustrated) the entire distance to a distal tip 74, and which includes no separate housing structure. The guide wire lumen 76 is formed through the distal tip of the catheter 70 and allows a guide wire 78 to pass through the tip and then outward along the exterior of the catheter. A second guide wire lumen is defined by a parallel tube 80 which is attached to the side of the catheter body 72. An ultrasonic transducer 82 is mounted on a rotating block 84 so that a conical imaging plane can be formed. The guide wire 78 passes through the conical imaging plane and defines an image artifact in the resulting ultrasonic image. An L-shaped insignia 86 is formed on the catheter body 72 proximally to the ultrasonic transducer. In this way, both the ultrasonic reference marker and the fluoroscopic reference marker of the present invention can be provided.

Figure 4:
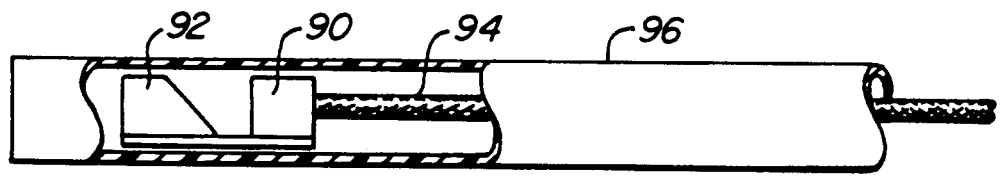
FIGS. 4 and 5 illustrate the distal end of a third embodiment of a catheter constructed in accordance with the principles of the present invention.
Figure 5:
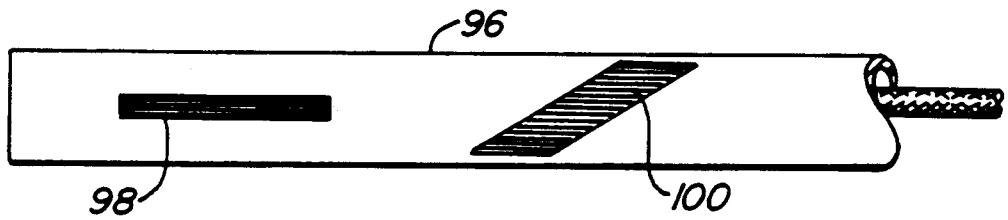

In a third embodiment of the present invention (FIGS. 4 and 5), a tandem assembly of a transducer 90 and mirror 92 are mounted at the distal end of a drive shaft 94. The transducer and mirror 90 and 92 may be inserted within a flexible exterior sheath 96, and images obtained by rotating the tandem assembly in a conventional manner. In order to provide the necessary ultrasonic reference marker, an ultrasonically opaque stripe 98 may be formed on the exterior of sheath 96 in the region proximate the tandem assembly of the ultrasonic transducer 90 and mirror 92. In this way, the stripe will pass through the image plane of the catheter. A fluoroscopic reference marker 100, in the form of an inclined stripe, is formed on the exterior of sheath 96 and is located proximally of the region in which the transducer 90 and mirror 92 will be located. In that way, the fluoroscopically-visible marker will be visible without interference from the imaging components.

Referring now to FIGS. 6A-C, 7A-C, and 8A-C, use of the catheter 10 in imaging a blood vessel BV is illustrated.

Figure 6A:
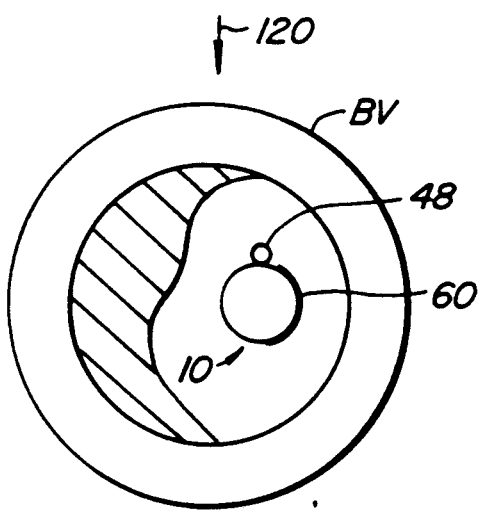

The catheter 10 is illustrated in different rotational orientations in each of the FIGS. 6A, 6B and 6C. In particular, the catheter 10 is illustrated with the bridge member 48 in the 12 o'clock position in FIG. 6A, in the 3 o'clock position in FIG. 6B, and in the 6 o'clock position in FIG. 6C. The catheter 10, could, of course, be in any rotational position since the catheter will undergo substantial torsional twisting and the rotational position of its distal end is therefore random when it reaches a region of interest within the vascular system.

Figure 8A:
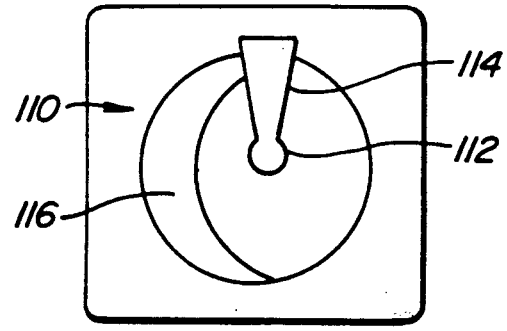

Referring now to FIG. 8A, an ultrasonic image 110 which generally corresponds to that which might be produced by the catheter 10 as oriented in FIG. 6A is illustrated. Note that the catheter itself is visible at 112 while the image artifact produced by the bridge member 48 is apparent as a shadow 114. The vessel lumen generally appears as a circle with stenotic material appearing as a shaded region 116 located generally on one side of the lumen. Based on the information in FIG. 8A, the viewing physician can determine that the catheter is oriented with the bridge element 48 directed at one edge of the stenotic material. The viewing physician, however, will not be able to determine the absolute rotational orientation of the image relative to the blood vessel. That is, it is not apparent from the information in the ultrasonic image whether or not the stenotic material is in reality on the left side of the blood vessel as it appears in the image, or is otherwise oriented.

Figure 7A:

By viewing the distal end of the catheter fluoroscopically, the orientation of the catheter 10 within the blood vessel lumen can be determined and this information used to determine the actual orientation of the ultrasonic image. The fluoroscopic stripe 60 is illustrated on the right hand side of the catheter 10 (as viewed in FIG. 6A). If the fluoroscopic image is produced from the direction shown by arrow 120, the stripe 60 will produce an image as illustrated in FIG. 7A. This V-shaped image or shadow is characteristic of the catheter 10 being viewed from the top, i.e., from the side in which the bridge 48 is located. Knowing that the bridge 48 is actually disposed upward, the treating physician can conclude that the image in FIG. 8A is rotationally correct, with the top of the stenotic region 116 actually being at the top of the blood vessel as the patient reclines.

The apparent ultrasonic image, however, will not always be rotationally correct. For example, in the same blood vessel BV having the same stenotic lesion therein, should the catheter 10 be oriented with the bridge in the 3 o'clock position, as illustrated in FIG. 6B, the apparent ultrasonic image will be as illustrated in FIG. 8B, with the shadow 114 still directed upward (assuming that the electronic circuitry scans so that the image artifact is always arranged vertically), but the stenotic material will appear to be shifted in the counterclockwise direction by 90° when compared to the image in FIG. 8A. Such a shift, however, can be accounted for by observing the inclined stripe 60 under the fluoroscope. The pattern illustrated in FIG. 7B is characteristic of the catheter 10 being oriented with bridge 48 being in the 3 o'clock position. Knowing this, the viewing physician will realize that the actual top of the ultrasonic image is 90° in the counterclockwise direction from shadow 114.

A similar situation is illustrated in FIGS. 6C, 7C, and 8C, where the catheter 10 is inverted by 180° relative to the rotational orientation in FIG. 6A. There, the ultrasonic image is also rotated by 180°, but such rotation is apparent in view of the orientation of stripe 60 when viewed fluoroscopically, as illustrated in FIG. 7C.

Although the foregoing invention has been described in detail for purposes of clarity of understanding, it will be obvious that certain modifications may be practiced within the scope of the appended claims.

What is claimed is:

1. An ultrasonic imaging catheter comprising:
a catheter body having a proximal end and a distal end;
means within the distal end of the catheter body for producing an ultrasonic cross-sectional image in an image plane generally normal to the longitudinal axis of the catheter body;
means for producing a marker on the ultrasonic cross-sectional image, where the position of the marker corresponds to the rotational orientation of the distal end of the catheter at the time the image is produced; and
means on the catheter body for producing a fluoroscopically visible marker which is in a fixed relative rotational alignment with the ultrasonic image marker, whereby the orientation of the ultrasonic image may be correlated with the physical orientation of the catheter body observed by fluoroscopy.

2. An ultrasonic imaging catheter as in claim 1, wherein the means for producing an ultrasonic cross-sectional image comprises a fixed ultrasonic transducer and a rotatable mirror disposed to reflect a signal from the transducer radially outward.

3. An ultrasonic imaging catheter as in claim 1, wherein the means for producing an ultrasonic cross-sectional image comprises a rotatable assembly including an ultrasonic transducer and a mirror arranged in tandem with the mirror disposed to reflect a signal from the transducer radially outward.

4. An ultrasonic imaging catheter as in claim 1, wherein the means for producing an ultrasonic cross-sectional image comprises a rotatable ultrasonic transducer.

5. An ultrasonic imaging catheter as in claim 1, wherein the means for producing an ultrasonic marker comprises an ultrasonically opaque element fixed to the catheter body and passing through the image plane.

6. An ultrasonic imaging catheter as in claim 1, wherein the means for producing a fluoroscopically visible marker comprises a fluoroscopically visible geometric pattern which is spaced longitudinally from the ultrasonic imaging means and which produces a pattern which is uniquely characteristic of a particular rotational orientation of the catheter body.

7. An ultrasonic imaging catheter comprising:
a catheter body having a proximal end and a distal end;
means within the distal end of the catheter body for producing an ultrasonic cross-sectional image in an image plane generally normal to the longitudinal axis of the catheter body;
an ultrasonically opaque element fixed relative to the catheter body and passing through the image plane;
a fluoroscopically opaque marker formed on the catheter body and spaced longitudinally apart from the ultrasonic imaging means, wherein said marker when viewed in a direction normal to the longitudinal axis of the catheter body produces a pattern which is uniquely characteristic of a particular rotational orientation of the catheter body.

8. An ultrasonic imaging catheter as in claim 7, wherein the means for producing an ultrasonic cross-sectional image comprises a fixed ultrasonic transducer and a rotatable mirror disposed to reflect a signal from the transducer radially outward.

9. An ultrasonic imaging catheter as in claim 8, further comprising a substantially rigid housing having a distal compartment holding the ultrasonic transducer and a proximal compartment holding the rotatable mirror, wherein the image plane is located in a gap between the distal and proximal compartments and the ultrasonically opaque element is a strut member which rigidly joins the distal and proximal compartments together.

10. An ultrasonic imaging catheter as in claim 9, wherein the strut member is axially aligned with the catheter body.

11. An ultrasonic imaging catheter as in claim 12, wherein the strut member is a tube which is aligned to carry a movable guide wire.

12. An ultrasonic imaging catheter as in claim 7, wherein the means for producing an ultrasonic cross-sectional image comprises a rotatable assembly including an ultrasonic transducer and a mirror arranged in tandem with the mirror disposed to reflect a signal from the transducer radially outward.

13. An ultrasonic imaging catheter as in claim 7, wherein the means for producing an ultrasonic cross-sectional image comprises a rotatable ultrasonic transducer.

14. An ultrasonic imaging catheter as in claim 7, wherein the fluoroscopically opaque marker is a stripe formed on the outside of the catheter body.

15. An ultrasonic imaging catheter as in claim 14, wherein the stripe is a spiral arc.

16. An ultrasonic imaging catheter as in claim 14, wherein the stripe has an L-shaped geometry.

17. A method for correlating the rotational orientation of an ultrasonic image produced by a catheter with the rotational orientation of the catheter itself observed by fluoroscopy, said method comprising:
producing an ultrasonic cross-sectional image in an image plane generally normal to the longitudinal axis of the catheter, said image having a marker which is aligned with a fixed radial direction in the image plane relative to the catheter;
producing a fluoroscopic image of the catheter in a plane generally parallel to the longitudinal axis of the catheter, wherein the catheter has a fluoroscopic marker which is aligned in a predetermined orientation relative to the ultrasonic marker, whereby the rotational orientation of the catheter can be correlated with the rotational orientation of the ultrasonic image.

18. A method as in claim 17, wherein the ultrasonic cross-sectional image is produced by mechanically rotating an ultrasonic transducer or a mirror which reflects a signal from an ultrasonic transducer.

19. A method as in claim 17, wherein the ultrasonic cross-sectional image is produced by a phasedarray of ultrasonic transducers.

20. A method as in claim 17, wherein the ultrasonic marker is produced by an ultrasonically opaque element fixed relative to the catheter and passing through the image plane.

21. A method as in claim 17, wherein the ultrasonic marker is produced electronically.

22. A method as in claim 17, wherein the fluoroscopic marker is produced by a fluoroscopically opaque stripe present on the catheter and having a geometry selected to produce a unique pattern for each rotational orientation of the distal end of the catheter.

23. A method as in claim 22, wherein the opaque stripe is a spiral arc.

24. A method as in claim 22, wherein the opaque stripe has an L-shaped geometry.

25. A method for producing a cross-sectional image of the interior of a blood vessel, said marker comprising:
introducing the distal end of a catheter to a desired region within the blood vessel;
mechanically rotating an ultrasonic signal about an image plane which is normal to the distal end of the catheter;
receiving reflected ultrasonic signal from the interior of the blood vessel and producing an ultrasonic cross-sectional image therefrom;
producing a marker in the ultrasonic cross-sectional image which is aligned with a fixed radial direction in the image plane;
fluoroscopically imaging the distal end of the catheter in a plane generally normal to the image plane; and
producing a marker in the fluoroscopic image which corresponds to the rotational alignment of the catheter in the blood vessel, whereby the rotational orientation of the catheter can be correlated with the rotational orientation of the ultrasonic image.

26. A method as in claim 25, wherein the ultrasonic marker is produced by an ultrasonically opaque element fixed relative to the catheter and passing through the image plane.

27. A method as in claim 25, wherein the ultrasonic marker is produced electronically.

28. A method as in claim 25, wherein the ultrasonic marker is produced by disrupting the rotation of the ultrasonic signal at the same rotational position each revolution.

29. A method as in claim 25, wherein the fluoroscopic marker is produced by a fluoroscopically opaque stripe present on the catheter and having a geometry selected to produce a unique pattern for each rotational orientation of the distal end of the catheter.

30. A method as in claim 29, wherein the opaque stripe is a spiral arc.

31. A method as in claim 29, wherein the opaque stripe has an L-shaped geometry.

* * * * *